(12) United States Patent
Petty et al.

(10) Patent No.: US 7,512,436 B2
(45) Date of Patent: Mar. 31, 2009

(54) METHOD OF EVALUATING METABOLISM OF THE EYE

(75) Inventors: Howard R. Petty, Livonia, MI (US); Victor M. Elner, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 523 days.

(21) Appl. No.: 10/777,423

(22) Filed: Feb. 12, 2004

(65) Prior Publication Data
US 2005/0182327 A1 Aug. 18, 2005

(51) Int. Cl.
*A61B 3/12* (2006.01)

(52) U.S. Cl. .................. 600/476; 600/473; 600/558; 351/205; 351/206; 351/211; 351/213; 351/221

(58) Field of Classification Search .............. 600/317, 600/473, 476, 558; 351/205, 206, 211, 213, 351/221
See application file for complete search history.

(56) References Cited

U.S. PATENT DOCUMENTS

| | | | |
|---|---|---|---|
| 4,569,354 A * | 2/1986 | Shapiro et al. ............. 600/476 |
| 6,013,034 A * | 1/2000 | Fernandes Da Cunha Vaz et al. ...................... 600/476 |
| 6,236,881 B1 * | 5/2001 | Zahler et al. ............... 600/476 |
| 6,370,422 B1 * | 4/2002 | Richards-Kortum et al. 600/478 |
| 6,371,615 B1 * | 4/2002 | Schweitzer et al. ......... 351/221 |
| 6,478,424 B1 * | 11/2002 | Grinvald et al. ............ 351/206 |
| 6,556,853 B1 * | 4/2003 | Cabib et al. ................ 600/407 |
| 2002/0133080 A1 * | 9/2002 | Apruzzese et al. .......... 600/477 |
| 2003/0004418 A1 * | 1/2003 | Marmorstein ............. 600/475 |
| 2005/0010115 A1 * | 1/2005 | Bone et al. ................. 600/476 |
| 2005/0065436 A1 * | 3/2005 | Ho et al. .................... 600/431 |
| 2005/0159662 A1 * | 7/2005 | Imanishi et al. ............ 600/473 |
| 2005/0208103 A1 * | 9/2005 | Adamis et al. ............. 424/427 |

OTHER PUBLICATIONS

Abiko et al., Relationship between autofluorescence and advanced glycation end products in diabetic lenses. 1999. Exp Eye Res. 68:361-6 (Academic Press, Asahikawa, Japan).

Abler A.S., Photic injury triggers apoptosis of photoreceptor cells. 1996. Res Commun Mol Pathol Pharmacol. 92:177-89 (PJD Publications, Westbury, NY, USA).

(Continued)

*Primary Examiner*—Brian L. Casler
*Assistant Examiner*—Baisakhi Roy
(74) *Attorney, Agent, or Firm*—Marshall, Gerstein & Borun LLP

(57) ABSTRACT

A method and apparatus for measuring the retinal auto-fluorescence of a subject retina includes an excitation light source for providing an excitation light at a wavelength of at least 450 nm and an image capture device for recording an ocular auto-fluorescence signal generated in response to the excitation light. The image capture device includes a filter for reducing background non-signal wavelengths from the ocular auto-fluorescence signal and an image intensifier for increasing the ocular auto-fluorescence signal strength. The method and apparatus may further include a processor that analyzes the ocular auto-fluorescence signal to determine a contrast change or pattern to thereby detect retinal disease or damage. The processor may compare the images with control images, past images of the same eye or other diagnostic modalities such as fundus photography, angiography, or visual field testing to detect the retinal disease or damage.

32 Claims, 4 Drawing Sheets

OTHER PUBLICATIONS

Adachi et al.,.Aberrant neutrophil trafficking and metabolic oscillations in severe pyoderma gangrenosum. 1998. J Invest Dermatol. 111:259-68 (Detroit, MI, USA).

Adachi et al.,.Amplitude and frequency modulation of metabolic signals in leukocytes: synergistic role in interferon-γ and Interleukin-6-mediated cell activation. 1999. J Immunol. 163:4367-74 (Bethesda, MD, USA).

Amit et al., Complement deposition on immune complexes diminishes the frequencies of metabolic, proteolytic and superoxide oscillations of migrating neutrophils. 1999. Cell Immunol. 194:47-53 (Academic Press, Detroit, MI, USA).

Berkertaar et al., Axotomy results in delayed death and apoptosis of retinal ganglion cells in adult rats. 1994. J Neurosci. 14:4368-74 (Society for Neuroscience, Montreal. Quebec, Canada).

Brunk et al., Lipofuscin: mechanisms of age-related accumulation and influence on cell function. 2002. Free Radical Biol Med. 33:611-9 (Elsevier Science, Inc., Linköping, Sweden, printed in USA).

Buchi E. R., Cell death in rat retina after pressure-induced ischaemia-reperfussion insult: electron microscopic study II. Outer nuclear layer. 1992. Jpn J Ophthalmol. 36:62-8 (Tokyo, Japan).

Buchi E.R., Cell death in the rat retina after a pressure-induced ischaemia-reperfusion insult: an electron microscopic study I. Ganglion cell layer and Inner nuclear layer. 1992. Exp Eye Res. 55:605-13 (Academic Press, Rockville, MD, USA).

Chader G.J., Animal models in research on retinal degenerations: past progress and future hope. Vision Res. 42:393-9 (Elsevier Science Ltd., Owing Mills, MD, USA).

Chance et al., Intrinsic fluorescence emission from the cornea at low temperatures: evidence of mitochondrial signals and their differing redox states in epithelial and endothelial sides. 1978. Exp Eye Res. 26:111-7 (Philadelphia, Pa, USA).

Chang et al., Apoptosis: final common pathway of photoreceptor death in rd, rds and rhodopsin mutant mice. 1993. Neuron. 11:595-605 (Cell Press, Newton, Ma, USA).

Chiou et al., Apoptosis of human retina and retinal pigment cells induced by human cytomegalovirus infection. 2002. Opthalmic Res. 34:77-82 (S. Karger AG, Basel, Switzerland).

Coremans et al., (Semi-)quantitative analysis of reduced nicotinamide adenine dinucleotide fluorescence images of blood-perfused rat heart. 1997. Biophys J. 72:1849-60 (The Biophysical Society, Bethesda, MD, USA).

Danielson et al., Cells bearing mutations causing Leber's hereditary optic neuropathy are sensitized to Fas- Induced apoptosis. 2002. J Biol Chem. 277:5810-5 (The American Society for Biochemistry and Molecular Biology, Inc., Rockville, MD, USA).

Delori et al., In vivo fluocrescence of the ocular funds exhibits retinal pigment epithelium lipofuscin characteristics. 1995. Invest Opthalmol Vis Sci. 36:718-29 (Association for Research in Vision and Ophthalmology, Rockville, MD, USA).

Delori et al., Autofluorescence distribution associated with drusen in age-related macular degeneration. 2000. Invest Ophthalmol Vis Sci. 41:496-504 (Association for Research in Vision and Ophthalmology, Rockville, MD, USA).

Delori et al., Age-related accumulation and spatial distribution of lipofuscin in RPE of normal subjects. 2001. Invest Ophthalmol Vis Sci. 42:1855-66 (Association for Research in Vision and Ophthalmology, Rockville, MD, USA).

Delori et al., Macular pigment density measured by autofluorescence spectrometry: comparison with reflectometry and heterochromatic flicker photometry. 2001. J Opt Soc Am A. 18:1212-30 (Optical Society of America, Washington, D.C., USA).

Denis et al., Advanced glycation end-products induce apoptosis of bovine retinal pericytes in culture: involvement of diacylglycerol/ceramide production and oxidative stress induction. 2002. Free Radical Biology & Medicine. 33:236-47 (Elsevier Science Inc., Amsterdam, Netherlands).

Donovan et al., Caspase-independent photoreceptor apoptosis in vivo and differential expression of apoptotic protease activating factor-1 and caspase-3 during retinal development. 2002. Cell Death and Differentiation. 9:1220-31 (Natural Publishing Group, London, England).

Draganow et al., In situ evidence for DNA fragmentation in Huntingtons disease striatum and Alzheimers disease temporal lobes. 1995. Neuroreport. 6:1053-7 (Rapid Communications of Oxford Ltd., Oxford, England).

Dunaief et al., The role apoptosis in age-related macular degeneration. 2002. Arch Ophthalmol. 120:1435-42 (Chicago, IL, USA).

Elleder et al., Autofluorescence of melanins induced by ultraviolet radiation and near ultraviolet light. A histochemical and biochemical study. 2001. Histochem J. 33:273-81 (Kluwer Academic Publishers, Springer Verlag, Netherlands).

Gal et al., Mutations in MERTK, the human orthologue of the RCS rat retinal dystrophy gene, cause retinitis pigmentosa. 2000. Nature Genetics. 26:270-1 (Nature America Inc., New York, NY, USA).

Garcia et al., Apoptosis in adult retinal ganglion cells after axotomy. 1994. J Neurobiol. 25:431-8 (John Wiley & Sons, Inc., Hoboken, NJ, USA).

Garcia et al., Programmed call death of retinal ganglion cells during experimental glaucoma. 1995. Exp Eye Res. 61:33-44 (Academic Press Limited, Rockville, MD, USA).

Ghelli et al., Leber's hereditary optic neuropathy (LHON) pathogenic mutations induce mitochondrial-dependent apoptotic death in transmitochondrial cells incubated with galactose medium. 2003. J Biol Chem. 278:4145-50 (The American Society for Biochemistry and Molecular Biology, Inc., Rockville, MD, USA).

Goldblum et al., Prospects for relevant glaucoma models with retinal ganglion cell damage in the rodent eye. 2002. Vison Res. 42:471-8 (Elsevier Science Ltd., Bem, Switzerland).

Gordon et al., DNA damage and repair in light-induced photoreceptor degeneration. 2002. Invest Ophthalmol Vis Sci. 43:3511-21 (Association for Research in Vision and Ophthalmology, Rockville, MD, USA).

Hao et al., Evidence for two apoptotic pathways in light-induced retinal degeneration. 2002. Nature. 32:254:60 (Nature America Inc., New York, NY, USA).

Heiduschka et al., Aurintricarboxylic acid promotes survival and regeneration of axotomised retinal ganglion cells in vivo. 2000. Neuropharmacol. 39:889-902 (Elsevier Science Ltd., Mönster, Germany).

Hisatomi et al., Critical role of photoreceptor apoptosis in functional damage after retinal detachment. 2002. Curr Eye Res. 24:161-72 (Swets & Zeitlinger, Lisse, Netherlands).

Holz et al., Fundus autofluorescence and development of geographic atrophy in age-related macular degeneration. 2001. Invest Ophthalmol Vis Sci. 42:1051-6 (Association for Research in Vision and Ophthalmology, Rockville, MD, USA).

Holz et al., Patterns of Increased in vivo fundus autofluorescence in the junctional zone of geographic atrophy of the retinal pigment epithelium associated with age-related macular degeneration. 1999. Graefe's Arch Clin Exp Ophthalmol. 237:145-52 (Springer-Verlag, Berlin, Germany).

Jones et al., Analysis of differentially expressed genes in retinitis pigmentosa retinas: altered expression of clusterin mRNA. 1992. FEBS Lett. 300:279-82 (Elsevier Science Publishers, Amsterdam, Netherlands).

Kaneda et al., Apoptotic DNA fragmentation and upregulation of Bax induced by transient ischemia of the rat retina. 1999. Brain Res. 815:11-20 82 (Elsevier Science Publishers, Amsterdam, Netherlands).

Katai et al., Apoptotic retinal neuronal death by ischemia-reperfusion is executed by two distinct caspase family proteases. 1999. Invest Ophthalmol Vis Sci. 40:2697-705 (Association for Research in Vision and Ophthalmology, Rockville, MD, USA).

Kayatz et al., Oxidation causes melanin fluorescence. 2001. Investigative Ophthalmol Vis Sci. 42:241-6 (Association for Research in Vision and Ophthalmology, Rockville, MD, USA).

Kerr et al., Apoptosis, a basic biological phenomenon with wider implications in tissue kinetics. 1972. Br J Cancer. 26:239-45 development. 2002 (Nature Publishing Group, .London, England).

Kerrigan et al., Tunel-positive ganglion cells in human primary open-angle glaucoma. 1997. Arch Ophthalmol. 115:1031-5 (Chicago, IL, USA).

Kidd, Proteolytic activities that mediate apoptosis. 1998. Annu Rev Physiol. 60:533-73 (Annual Reviews, Palo Alto, CA, USA).

Kindzelskii et al., Proximity oscillations of complement receptor type 4 and urokinase receptors on migrating neutrophils are linked with signal transduction/metabolic oscillations. 1997. Biophys J. 73:1777-84 (The Biophysical Society, Bethesda, MD, USA).

Kindzelskii et al., Pregnancy alters glucose-6-phosphate dehydrogenase trafficking, cell metabolism and oxidant release of maternal neutrophils. 2002. J Clin Invest. 110:1801-11 (Ann Arbor, MI, USA).

Kindzelskii et al., Apparent role of traveling metabolic waves in periodic oxidant release by living cells. 2002. Proc Natl Acad Sci USA. 99:9207-12 (Melville, NY, USA).

Kindzelskii et al., Extremely low frequency electric fields promote neutrophil extension, metabolic resonance and DNA damage during migration. 2000. Biochim Biophys Acta. 1495:90-111 (Elsevier Science Publishers, Netherlands).

Kindzelskii et al., Oscillatory pericellular proteolysis and oxidant deposition during neutrophil migration. 1998. Biophys J. 74:90-7 (The Biophysical Society, Bethesda, MD, USA).

Kowluru et al., Diabetes-induced activation of caspase-3 in retina: effect of antioxidant therapy. 2002. Free Radic Res. 36:993-9. (Taylor & Francis, Ltd., Abdingdon, Oxfordshire, England).

Kunz et al., Flow cytometric detection of mitochondrial dysfunction in subpopulations of human mononuclear cells. 1997. Anal Biochem. 246:218-24 (Academic Press, Rockville, MD, USA).

Kunz et al., Functional Imaging of mitochondrial redox state. 2002. Methods in Enzymology. 352:135-150 (Elsevier Science USA, Orlando, FL, USA).

Kunz et al., Quantification of the content of fluorescent flavoproteins in mitochondria from liver, kidney cortex, skeletal muscle, and brain. 1993. Biochem Med Metabolic Biol. 50:103-10. (Academic Press, Rockville, MD, USA).

Kunz et al., Contribution of different enzymes to flavoprotein fluorescence of isolated rat liver mitochondria. 1985. Biochimica et Biophysica Acta. 841:237-46 (Elsevier Science Publishers, Amsterdam, Netherlands).

Kunz et al., Functional characterization of mitochondrial oxidative phosphorylation in saponin-skinned human muscle fibers. 1993. Biochimica Biophysica Acta. 1144:46-53 46 (Elsevier Science Publishers, Amsterdam, Netherlands).

Kunz et al., Measurement of fluorescence changes of NAD(P)H and of fluorescent flavoproteins in saponin-skinned human skeletal muscle fibers. 1994. Anal Biochem. 216:322-7 (Academic Press, Rockville, MD, USA)..

Kunz, Spectral properties of fluorescent flavoproteins of isolated rat liver mitochondria. 1986. FEBS Lett. 195:92-6 (Elsevier Science Publishers, Amsterdam, Netherlands).

Kuroiwa et al., Expression of cell cycle-related genes in dying cells in retinal ischemic injury. 1998. Invest Ophthalmol Vis Sci. 39:610-7 (Association for Research in Vision and Ophthalmology, Rockville, MD, USA).

Kuznetsov, et al., Functional imaging of mitochondria in saponin-permeabilized mice muscle fibers. 1998. J Cell Biol. 140:1091-9 (The Rockefeller University Press, New York, NY, USA).

La Vail, Legacy of the RCS rat: impact of a seminal study on retinal cell biology and retinal degenerative diseases. 2001. Prog Brain Res. 131:617-27 (Elsevier Science BV, Amsterdam, Netherlands).

Lam et al., N-methyl-D-aspartate (NMDA)-induced apoptosis in rat retina. 1999. Invest Ophthalmol Vis Sci. 40:2391-7(Association for Research in Vision and Ophthalmology, Rockville, MD, USA).

Lam et al. Apoptosis and caspases after ischemia-reperfusion injury in rat retina. 1999. Invest Ophthalmol Vis Sci. 40:967-975 (Association for Research in Vision and Ophthalmology, Rockville, MD, USA).

Li W et al., Altered mRNA levels of antioxidant enzymes in pre-apoptotic pericytes from human diabetic retinas. 1999. Cell Mol Biol. 45:59-66 (Frances).

Liang et al., Imaging neutrophil activation: analysis of the translocation and utilization of NAD(P)H-associated autofluorescence during antibody-dependent target oxidation. 1992. J Cell Physiol. 152:145-56 (Wiley-Liss, Inc., Hoboken, NJ, USA).

Lipton et al., Excitatory amino acids as a final common pathway for neurologic disorders. 1994. N Engl J Med. 330:613-622 (Boston, MA, USA).

Lois, et al., Quantitative evaluation of fundus autofluorescence imaged "in vivo " in eyes with retinal disease. 2000. Br J Ophthalmol. 84:741-5 (Bristol, England).

Lois, et al., Fundus autofluorescence in patients with age-related macular degeneration and high risk of visual loss. 2002. Am J Ophthalmol. 133:341-9 (Elsevier Science Inc., USA, Orlando, FL, USA).

Lolley et al., Linkage of photoreceptor degeneration by apoptosis with inherited defect in phototransduction. 1994. Invest Ophthalmol Vis Sci. 35:358-62 (Association for Research in Vision and Ophthalmology, Rockville, MD, USA).

Marrnorstein et al., Spectral profiling of autofluorescencee associated with lipofuscion, Bruch's membrane, and sug-RPE deposits in normal and AMD eyes. 2002. Investigative Ophthalmol Vis Sci. 43:2435-41 (Association for Research in Vision and Ophthalmology, Rockville, MD, USA).

Marsden, et al., Control of apoptosis in the immune system: Bcl-2, BH3-only proteins and more. 2003. Annu Rev Immunol. 21:71-105 (Annual Reviews, Palo Alto, CA, USA).

Masters, Noninvasive corneal redox fluorometry. 1984. Curr Topics Eye Res. 4:139-200 (Academic Press, Inc., USA)..

McKinnon, et al., Caspase activation and amyloid precursor protein cleavage in rat ocular hypertension. 2002. Invest Ophthalmol Vis Sci. 43:1077-87 (Association for Research in Vision and Ophthalmology, Rockville, MD, USA).

Mittag, et al. Retinal damage after 3 to 4 months of elevated intraocular pressure in a rat glaucoma model. 2000. Invest Ophthalmol Vis Sci. 41:3451-9 (Association for Research in Vision and Ophthalmology, Rockville, MD, USA)..

Mizutani et al. Accelerated death of retinal microvascular cells in human and experimental diabetic retinopathy. 1996. J Clin Invest . 97:2883-90 (Ann Arbor, MI, USA).

Mohr et al., Caspase activation in retinas of diabetic and galactosemic mice and diabetic patients. 2002. Diabetes. 51:1172-9 (The American Diabetes Association, Alexandria, VA, USA).

Mori et al., Changes in corneal and lens autofluorescence and blood glucose levels in diabetics: parameters of blood glucose control. 1997. Curr Eye Res. 16:534-8 (Oxford University Press, Oxford, England).

Naskar et al., Detection of early neuron degeneration and accompanying microglial responses in the retina of a rat model of glaucoma. 2002. Invest Ophthalmol Vis Sci. 43:2962-8. (Association for Research in Vision and Ophthalmology, Rockville, MD, USA).

Newell, Ophthalmology: Principles and Concepts. 1982. (C.V. Mosby Co., St. Louis., MO, USA).

Nickells, Apoptosis of retinal ganglion cells in glaucoma: an update of the molecular pathways involved in cell death. 1999. Surv Ophthalmol. 43:S151-S161 (Elsevier Science Inc., Orlando, FL, USA).

Nijhawan et al., Apoptosis in neural development and disease. 2000. Annu Rev Neutrosci. 23:73-87 (Annual Reviews, Palo Alto, CA, USA).

Olsen et al., A model of the oscillatory metabolism of activated neutrophils. 2003. Biophys J. 84:69-81 (The Biophysical Society, Bethesda, MD, USA).

Oppenheim, Cell death during development of the nervous system. 1991. Annu Rev Neurosci. 14:453-501 (Annual Reviews, Palo Alto, CA, USA).

O'Rourke, Oscillations of membrane current and excitability driven by metabolic oscillations in heart cells. 1994. Science. 265:962-6 (Washington, D.C., USA).

Oshitari, The role of c-fos in cell death and regeneration of retinal ganglion cellls. 2002. Invest Ophthalmol Vis Sci. 43:2442-9 (Association for Research in Vision and Ophthalmology, Rockville, MD, USA).

Petty et al., High-speed imaging of sustained metabolic target patterns in living neutrophils during adherence. 2000. J Phys Chem B 104:10952-55 (American Chemical Society, Washington, D.C., USA).

Petty et al., Dissipative metabolic patterns respond during neutrophil transmembrane signaling. 2001. Proc Natl Acad Sci USA. 98:3145-9. (Washington, D.C., USA).

Petty et al., Imaging sustained dissipative patterns in the metabolism of individual living cells. 2000. Physical Rev Lett. 84:2754-7 (The American Physical Society, College Park, MD, USA).

Petty et al., Neutrophil oscillations: temporal and spatiotemporal aspects of cell behavior. 2001. Immunologic Res. 23:125-34 (Humana Press Inc., Totowa, NJ, USA).

Petty et al., Oscillatory signals in migrating neutrophils: effects of time-varying chemical and electrical fields. 2000. In: Self-Organized Biological Dynamics and Nonlinear Control by External Stimuli, pp. 173-192 (J. Walleczek, ed., Cambridge University Press, Cambridge, England).

Podesta et al., Bax is increased in the retina of diabetic subjects and in associated with pericyte apoptosis in vivo and in vitro. 2000. Am J Pathol. 156:1025-32 (American Society for Investigative Pathology, Bethesda, MD, USA).

Portera-Cailliau, Apoptotic photoreceptor cell death in mouse model of retinitis pigmentosa. 1994. Proc Natl Acad Sci USA. 91:974-8 (PNAS, New York, NY, USA).

Quigley et al., Retinal ganglion cell death in experimental glaucoma and after axotomy occurs by apoptosis 1995. Invest Ophthalmol Vis Sci. 36:774-86 (Association for Research in Vision and Ophthalmology, Rockville, MD, USA).

Romashko et al., Subcellular metabolic transients and mitochondrial redox waves in heart muscle. 1998. Proc Natl Acad Sci USA. 95:1618-23 (PNAS, New York, NY, USA).

Romeo et al., Activation of nuclear factor-$\kappa$B induced by diabetes and high glucose regulates a proapoptotic program in retinal pericytes. 2002. Diabetes. 51:2241-8 (The American Diabetes Association, Alexandria, VA, USA).

Rosenbaum et al., Retinal ischemia leads to apoptosis which is ameliorated by aurintricarboxlic acid. 1997. Vision Res. 37:3445-51 (Elsevier Science Ltd., GB).

Rosenspire et al., Cutting edge: febrile temperatures dramatically enhance local oxidant release by adherent neutrophils in response to lipopolysaccharide. 2002. J Immunol. 169:5396-400 (The American Association of Immunologists, Inc., Rockville, MD, USA).

Rosenspire et al., Interferon-$\gamma$ and sinusoidal electric fields signal by modulating NAD(P)H oscillations in polarized neutrophils. 2000. Biophys J. 79:3001-8 (The Biophysical Society, Bethesda, MD, USA).

Rosenspire et al., Pulsed DC electric fields couple to natural NAD(P)H oscillations in HT 1080 fibrosarcoma cells. 2001. J Cell Sci. 114:1515-26 (The Company of Biologists Ltd., Cambridge, England).

Roth et al., Measurement of purine nucleoside concentration in the intact rat retina. 1996. J Neurosci Meth. 68:87-90 (Elsevier Science, BV, Amsterdam, Netherlands).

Roth et al., Concentrations of adenosine and its metabolites in the rat retina/choroids during reperfusion after ischemia. 1997. Curr Eye Res. 16:875-885 (Oxford University Press, Oxford, England).

Rudin et al., Apoptosis and disease; regulation and clinical relevance of programmed cell death. 1997. Annu Rev Med. 48:267-81 (Annual Reviews Inc., Palo Alto, CA, USA).

Sadun et al., Leber's hereditary optic neuropathy differentially affects smaller axons in the optic nerve. 2000. Trans Am Ophthalmol Soc. 98:223-32, (The American Ophthalmological Society, San Francisco, CA, USA).

Schachat et al., vol. 2. 1989. (C.V. Mosby Co., St. Louis, MO, USA). Information sheet for C101.

Schmitz-Valckenberg et al., Analysis of digital scanning laser ophthalmoscopy fundus autofluorescence images of geographic atrophy in advanced age-related macular degeneration. 2002. Graefe's Arch Clin Exp Ophthalmol. 240:73-8 (Springer-Verlag, Berlin, Germany).

Scholz et al., Flavin and pyridine nucleotide oxidation-reduction changes in perfused rat liver. 1. Anoxia and subcellular localization of fluorescent flavoproteins. 1969. J Biol Chem. 244:2317-24 (The American Society for Biochemistry and Molecular Biology, Inc., Rockville, MD, USA).

Schweitzer et al., Die altersabhangige makulopathie. Vergleichende untersuchungen swischen patienten, deren kindem und augengesunden. 2000. Ophthalmologe. 97:84-90 (Springer-Verlag, Heidelberg, Germany).

Seme et al., Differential recovery of retinal function after mitochondrial inhibition by methanol intoxication. Invest Ophthalmol Vis Sci. 2001. 42:834-41 (Association for Research in Vision and Ophthalmology, Rockville, MD, USA).

Shiino et al., Three-dimensional redox image of the normal gerbil brain. 1999. Neurosci. 91:1581-5 (Elsevier Science Ltd., GB).

Shimazaki et al., Distribution of autofluorescence in the rabbit corneal epithelium. 1993. Ophthalmic Res. 25:220-6 (S. Karger AG, Basel, Switzerland).

Shirvan et al., Anti-semaphorin 3A antibodies rescue retinal ganglion cells from cell death following optic nerve axotomy. 2002. J Biol Chem. 277:49799-807 (The American Society for Biochemistry and Molecular Biology, Inc., Rockville, MD, USA).

Solbach et al., Imaging of retinal autofluorescence in patients with age-related macular degeneration. 1997. Retina. 17:385-9 (Lippincott, Williams & Wilkins, Philadelphia, PA, USA).

Strasser et al., Apoptosis Signaling. 2000. Annu Rev Biochem. 69:217-45 (Annual Reviews, Palo Alto, CA, USA).

Tatton et al., Maintaining mitochondrial membrane impermeability: an opportunity for new therapy in glaucoma. 2001. Surv Ophthalmol. 45:S277-83 (Elsevier Science Inc., Amsterdam, Netherlands).

Tatton et al., Apoptotic mechansims in neurodegeneration: possible relevance to glaucoma. 1999. Eur J Ophthalmol. 9 Suppl 1:S22-9 (Wichtig Editore, Milan, IT).

Thanos et al., In vivo FM: using conventional fluorescence microscopy to monitor retinal neuronal death in vivo. 2002. Trends Neurosci. 25:441-4 (Elsevier Science Ltd., Germany).

Travis, Human genetics '98: Apoptosis mechanisms of cell death in the inherited retinal degenerations. 1998. Am J Hum Genet. 62:503-8 (The American Society of Human Genetics, Bethesda, MD, USA).

Troost et al., Apoptosis in amylotrophic lateral sclerosis is not restricted to motor neurons. Bcl-2 expression is increased in unaffected post-central gyrus. 1995. Neuropathol Appl Neurobiol. 21:498-504 (Blackwell Science Ltd., Oxford, England).

Tsubota et al., Noninvasive metabolic analysis of preserved rabbit cornea. 1988. Arch Ophthalmol. 106:1713-7 (Brooklyn, NY, USA).

Tsubota et al., Noninvasive measurements of pyridine nucleotide and flavoprotein in the lens. 1987. Invest Ophthalmol Vis Sci. 28:785-9 (Association for Research in Vision and Ophthalmology, Rockville, MD, USA).

Tsubota et al., Metabolic changes in the corneal epithelium resulting from hard contact lens wear. 1992. Cornea. 11:121-6 (Raven Press, Ltd., NY, USA).

Vielhaber et al., Mitochondrial DNA abnormalities in skeletal muscle of patients with sporadic amyotrophic lateral sclerosis. 2000. Brain. 123:1339-48 (Oxford University Press, Oxford, England).

Von Ruckmann et al., Distribution of pigment epithelium autofluorescence in retinal disease state recorded in vivo and its change over time. 1999. Graefe's Arch Clin Exp Ophthalmol. 237:1-9 (Springer-Verlag, Berlin, Germany).

Von Ruckmann et al., In vivo fundus autofluorescence in macular dystrophies. 1997. Arch Ophthalmol. 115:609-15 (Brooklyn, NY, USA).

Von Ruckmann et al., Abnormalities of fundus autofluorescence in central serous retinopathy. 2002. Am J. Ophthalmol 133:780-6 (Elsevier Science Inc., Amsterdam, Netherlands).

Wiedemann et al., Impairment of mitochondrial function in skeletal muscle of patients with amyotrophic lateral sclerosis. 1998. J Neurol Sci. 156:65-72 (Elsevier Science BV, Amsterdam, Netherlands).

Wilson et al., Argon laser photocoagulation-induced modification of gene expression in the retina. 2003. Invest Ophthalmol Vis Sci. 44:1426-34 (Association for Research in Vision and Ophthalmology, Rockville, MD, USA).

Worth et al., Mercury inhibition of neutrophil activity: evidence of aberrant cellular signaling and incoherent cellular metabolism. 2001. Scand. J Immunol. 53:49-55 (Blackwell Publishing, Oxford, England).

Xu et al., Apoptosis in human retinal degenerations. 1996. Trans Am Ophthalmol Soc. 94:411-30 (The American Ophthalmological Society, San Francisco, CA, USA).

Zacs et al., Caspase activation in an experimental model of retinal detachment. 2003. Invest Ophthalmol Vis Sci. 44:1262-7 (Association for Research in Vision and Ophthalmology, Rockville, MD, USA).

Zhang et al., Apoptosis in the retina during MCMV retinitis in immunosuppressed BALB/c mice. 2002. J Clin Virol. 25:S137-47 (Elsevier Science BV, Amsterdam, Netherlands).

Zhang et al., Mouse model of optic neuropathy caused by mitochondrial complex I dysfunction. 2002. Neurosci Lett. 326:97-100 (Elsevier Science Ireland, Ltd., Dublin, Ireland).

International Preliminary Report on Patentability for International Application No. PCT/US2005/03837, dated Dec. 28, 2006.

International Search Report for International Application No. PCT/US2005/03837, dated Nov. 22, 2006.

Written Opinion for International Application No. PCT/US2005/03837, dated Nov. 22, 2006.

* cited by examiner

METHOD OF EVALUATING METABOLISM OF THE EYE

STATEMENT REGARDING FEDERALLY SPONSORED RESEARCH OR DEVELOPMENT

This invention was made with government support under CA074120 and EY009441, awarded by the National Institutes of Health. The government has certain rights in this invention.

TECHNICAL FIELD

The disclosed device generally relates to measuring characteristics within the retina. In particular, the device embodies a non-invasive, single image method and apparatus for measuring metabolic activity within the retina and optic nerve.

BACKGROUND

FIG. 1 illustrates an exemplary eye 10 including a cornea 20 and a lens 22 to focus and direct light onto a retina 30, which is the light detection and neural processing component of the eye 10. The retina 30 extends from the optic nerve 24, which is composed of retinal nerve fibers, near the posterior pole 26 of the eye 10 to the or a serrata 28 extremitfy near the anterior segment 32 of the eye 10. The retina 30 contains two types of photoreceptor cells, rods and cones, which generate electrical signals in response to light.

Failure of any retinal component may result in blindness. For example, total or partial blindness may be caused by a reduction in blood supply to the retina, which in turn, may be the result of diabetic retinopathy or ischemic events such as retinal vein occlusion. Research has shown that other causes of blindness such as cytomegalovirus retinitis, glaucoma, Leber's optic neuropathy, retina detachment, age-related macular degeneration, retinitis pigmentosa, or light induced blindness are commonly associated with the apoptotic, or programmed death of retina cells.

Apoptosis generally involves the activation of one or more apoptotic signaling pathways by intrinsic or extrinsic stimuli causing the selective degeneration of neurons. The onset of apoptosis has been linked to mitochondrial dysfunction (which is indicative of a change in cellular metabolic activity) characterized by the loss of mitochondrial integrity leading to the release of apoptotic mediators and the activation of enzymes and other pathways leading to cell death. These changes in mitochondrial integrity result in a gain or a loss of pro- and anti-apoptotic signals and have been linked to the retina disorders that result in 95% of the instances of irreversible blindness. Early detection of mitochondrial dysfunction can allow for diagnosis, treatment, and monitoring of these disorders.

Current diagnostic techniques used in routine eye examinations typically employ ophthalmoscopes to visually inspect the retina and tonometers to evaluate intraocular pressures. While ophthalmoscopes can be used to diagnose retinal degeneration, they are only effective after substantial damage has already occurred and do not provide any indication of mitochondrial activity. Tonometers indent the eye in order to determine changes in intraocular pressure that may result in glaucoma, retinal ganglion cell death, or ischemia. However, the correlation between intraocular pressure and disease is not robust, as evidenced by patients developing glaucomatous degeneration with low pressures and patients with high pressure remaining disease free. Furthermore, these older methods cannot be correctly interpreted in the presence of biomechanical artifacts such as abnormal corneal thickness due to, for example, natural variations, disease, myopia, or refractive corneal surgery.

U.S. Pat. No. 4,569,354 entitled "Method and Apparatus for Measuring the Natural Retinal Fluorescence" discloses a method and apparatus for determining oxygenation of the retina by measuring the fluorescence of flavoprotein in the retina. According to this patent, a spot of excitation light of a wavelength of about 450 nanometers (nm) is scanned across the retina, in response to which retina auto-fluorescence at a wavelength of about 520 nm is detected. In particular, retinal emission light is detected at two wavelengths of about 520 nm and 540 nm to allow for compensation with respect to absorption and transmission variables in the eye. To compensate for fluorescence of the lens of the eye, the center of the pupil is imaged onto scanning mirrors so that the scanning beam of excitation light pivots at the center of the eye lens. Because this method and apparatus scans a small area of the retina (i.e. a very limited number of pixels) at a time, the strength of the measured signal is extremely low, resulting in a measured signal having a low signal-to-noise (S/N) ratio and little, if any, accuracy. Further, the small scan area necessitates an extended procedure time to completely scan the retina, which further increases potential for error caused by eye movement due to natural instability of extraocular muscle tone, blood pulsation and light contamination. Because of the inherent inaccuracies of this method and device, it is unable to operate as an accurate diagnosis and monitoring system.

Accordingly, a device and method for measuring the metabolism of the eye is needed to address the shortcomings of the known diagnostic tools and methods discussed above. Specifically, a device and method for non-invasively measuring the metabolic activity of cells that increases the diagnostic accuracy and speed in detecting retinal disorders is needed.

SUMMARY

The method and apparatus disclosed herein provides a rapid and non-invasive clinical and experimental tool to measure directly the vitality of a retinal cell based on the auto-fluorescence of excited flavoprotein (FP) within the retinal mitochondria. The disclosed method and apparatus for measuring the retinal auto-fluorescence of a subject retina includes an excitation light source for providing an excitation light at a wavelength of approximately 450 nm and an image capture device for recording an ocular auto-fluorescence signal generated in response to the excitation light. The image capture device includes a filter for filtering out undesired wavelengths from the ocular auto-fluorescence signal and includes an image intensifier for increasing the ocular auto-fluorescence signal strength. The method and apparatus may further include a processor that analyzes the ocular auto-fluorescence signal to determine a contrast change or pattern and can compare serial readings taken at different times or dates. Salient objectives addressed by the device and method disclosed below include: fast procedure time, high accuracy, a direct correlation between retinal metabolic activity and the existence of a retinal disorder, and increased signal-to-noise ratio (S/N).

BRIEF DESCRIPTION OF THE DRAWINGS

For a more complete understanding of the disclosed device, reference should be made to the following detailed description and accompanying drawings wherein.

DETAILED DESCRIPTION

Cellular auto-fluorescence may be observed by measuring the emissions of endogenous flavoproteins (FPs) and NAD (P)H molecules. Previous laboratory studies and experiments have shown that cellular metabolic activity is related to the auto-fluorescence of both FP and NAD(P)H molecules. However, NAD(P)H excites and auto-fluoresces in the near ultraviolet range, which promotes cataracts and retinal damage and is, therefore, not suitable for use on living subjects. Therefore, FP auto-fluorescence is being evaluated using, for example, a brief blue excitation light that can be transmitted via the optical structures of the eye without risk of retinal damage. Previous studies have indicated that elevated levels of apoptotic activity correlates with reduced metabolic activity that increases FP auto-fluorescent intensity and reduced metabolic activity. Thus, a method and apparatus that measures the fluorescence of FP is useful in evaluating retinal metabolic activity in order to aid in the early detection and/or the prevention of blinding disorders.

Figure 2:
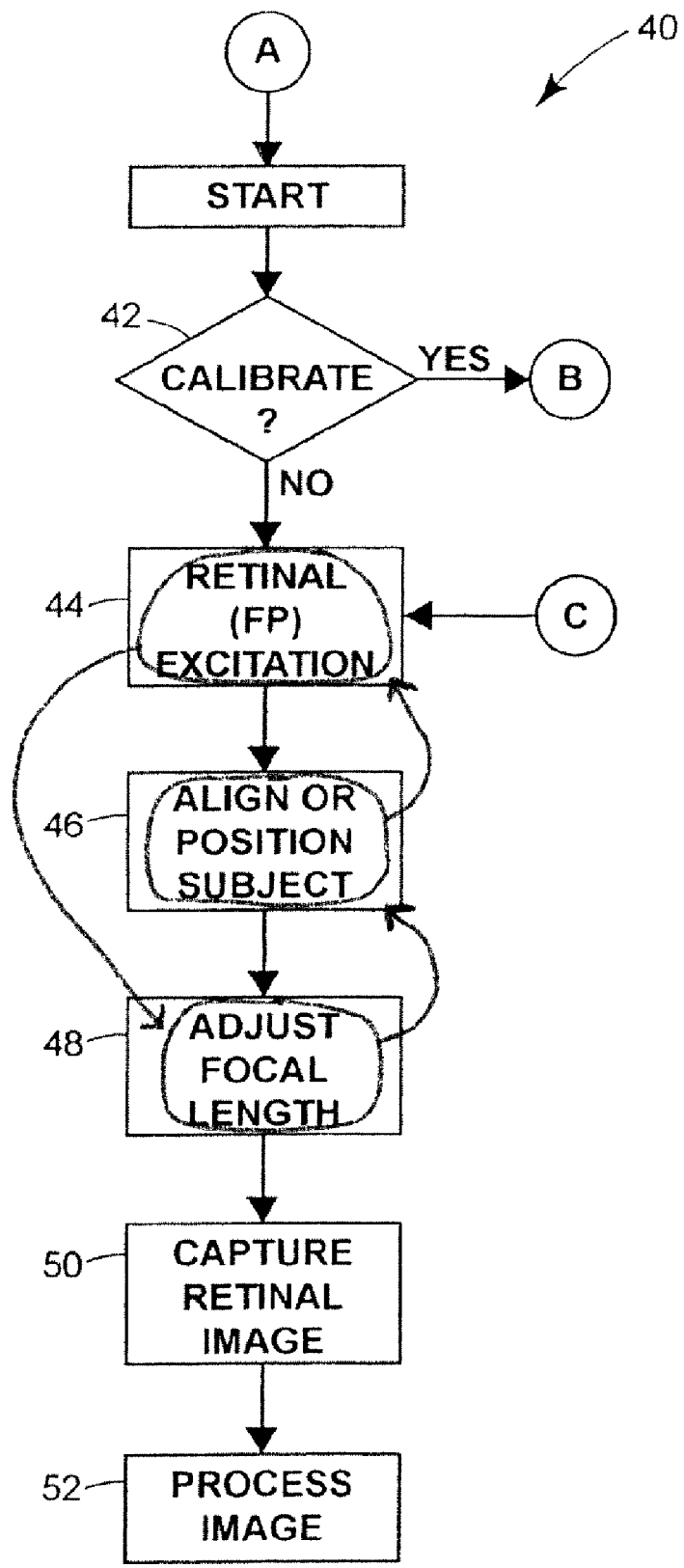
FIG. 2 illustrates a flowchart embodying the operation of an exemplary retinal testing and evaluation apparatus.

FIG. 2 illustrates a flowchart embodying one possible implementation of an exemplary retinal evaluation method 40. At a block 42, a calibration routine 60 (shown in more detail in FIG. 3), can be initiated either manually or upon the occurrence of some predefined condition. For example, the condition for implementing the calibration routine 60 may be based on the non-specific autofluorescence emitted from the eye, a database of autofluorescence images of the same eye examined previously, a database of control eyes imaged previously, a number of cycles or operations that the equipment has performed, the duration of time the equipment has been operating, the calculated mean time before failure (MTBF) of critical components, or any other identified criteria.

At a block 44, after the calibration routine 60 has been executed, skipped or otherwise completed, the subject to be evaluated can be positioned or aligned relative to the evaluation equipment. It will be understood that the alignment procedure may be accomplished in a variety of ways, such as employing a physical guide used on a desktop ophthalmoscope, fundus camera, or slit-lamp (not shown) to align the subject's head and retina with the equipment, a slit-lamp apparatus, or a retinal fundus camera apparatus. Further, the alignment procedure may be implemented using software by selecting the evaluation area of interest from a presented digital or graphical image. By selecting the area of interest, such as a retinal landmark like the optic disc or vascular patterns, the software may instruct a virtual camera aperture to focus or shift to the identified area of interest or may instruct physical elements within the system to shift and position into the desired or identified location.

At a block 46, a plurality of microscope objective lenses may be adjusted to a desired focal length. These adjustments may be made mechanically using, for example, a high precision rack and pinion arrangement to linearly shift the objective lens along the same line defined by the path of light generated by an excitation means, such as a light source. Further, it will be understood that the objective lens may be automatically positioned using a servo or positioning motor system to shift the lens to a predetermined position relative to the physical guide and the subject discussed in conjunction with the block 46. In addition, a range finder or pattern focusing technique (in which a pattern is projected into the optical path and an automatic focusing routine causes the pattern to become the system focal point) could be employed to allow the correct focal length to be automatically determined.

At a block 48, an excitation means, such as a light source, can be triggered or pulsed to stimulate the flavoproteins (FPs) associated with retinal mitochondria. Excitation may be initiated over a wide range of wavelengths using, for example, a He—Cd or argon-ion laser, and an incandescent or mercury lamp such as an ATTOARC™ variable intensity illuminator. However it is desirable to reduce potential signal noise by limiting the excitation spectrum to a range consistent with the excitation spectrum of FP, approximately 460 nm. To this end, an excitation filter such as an OMEGA OPTICAL® Model No. XF1012 (455DF70) excitation filter having a filter range of approximately 420-490 nm, may be used. The filtered excitation means stimulates the FP auto-fluorescence without stimulating additional molecules and thereby generating unwanted auto-fluorescence that could act as noise to degrade the overall accuracy of the evaluation technique. It will be understood that the excitation spectrum may be further limited by reducing the ambient light adjacent to the retina 30, which may be accomplished by reducing the testing room lighting, by fitting the subject with goggles, or any other similar method.

At a block 50, a single image representing the excited FP auto-fluorescence within the retina can be captured. For example, a high-speed charged coupled device (CCD) camera such as a PRINCETON INSTRUMENTS® PI-MAX ICCD model 512-Gen III camera can be employed to record an image of the auto-fluorescence of the retina. It will be understood that the field of view (FOV) of the CCD camera, with or without the magnification of the objective lens of the block 46, should be established to allow imaging of the retina (or any desired portion thereof) in a single picture.

One exemplary method of choosing an appropriate FOV to be imaged includes identifying retinal landmarks such as the optic disc or vascular patterns to use as aiming points and then adjusting the FOV to encompass the entire area of interest. Using an appropriate objective lens or lenses, the FP auto-fluorescence may be directed onto a CCD camera. After a set integration time, typically less than one second, the shutter is closed and the image is then downloaded to a computer. The captured digital images can be scanned visually or electronically to find areas of increased brightness, which may be diagnosed as apoptotic regions.

The CCD camera may further be augmented with a photon intensifier such as the above-identified PRINCETON INSTRUMENTS® image intensifier model Gen-III HQ that includes a photocathode for converting the image into an electrical signal. The electrical signal is multiplied and accelerated into a phosphor screen to produce an amplified image that may then be captured, stored and analyzed.

At a block 52, the captured amplified image can be analyzed, for example, by a program stored in a computer memory and executed on a processor, to evaluate the metabolic activity within the retina as indicated by the FP signal auto fluorescence. The captured image can be visually analyzed by an observer, trained or otherwise, to determine the presence or absence of patterns, changes or other aberrations of interest. However, as described above, it may also be desirable to automate the analysis procedure using the processor to execute image processing software. A software analysis program may analyze each pixel or element of the image to individually, and in conjunction with the surrounding pixels, determine local changes in contrast, rates of change in contrast and the existence of patterns. For example, the intensity of a single pixel or a group of pixels may be measured and compared to another adjacent pixel or group of pixels to determine the presence of local changes, patterns, or rates of change etc. which, in turn, can indicate a change in the health and function of the retina 30. The software analysis program may also correlate the captured metabolic image patterns with photography, angiograms, or visual fields corresponding to the same retinal regions. In addition, the program may analyze historical or other stored digital images and compare them to recent or time elapsed images.

Figure 3:
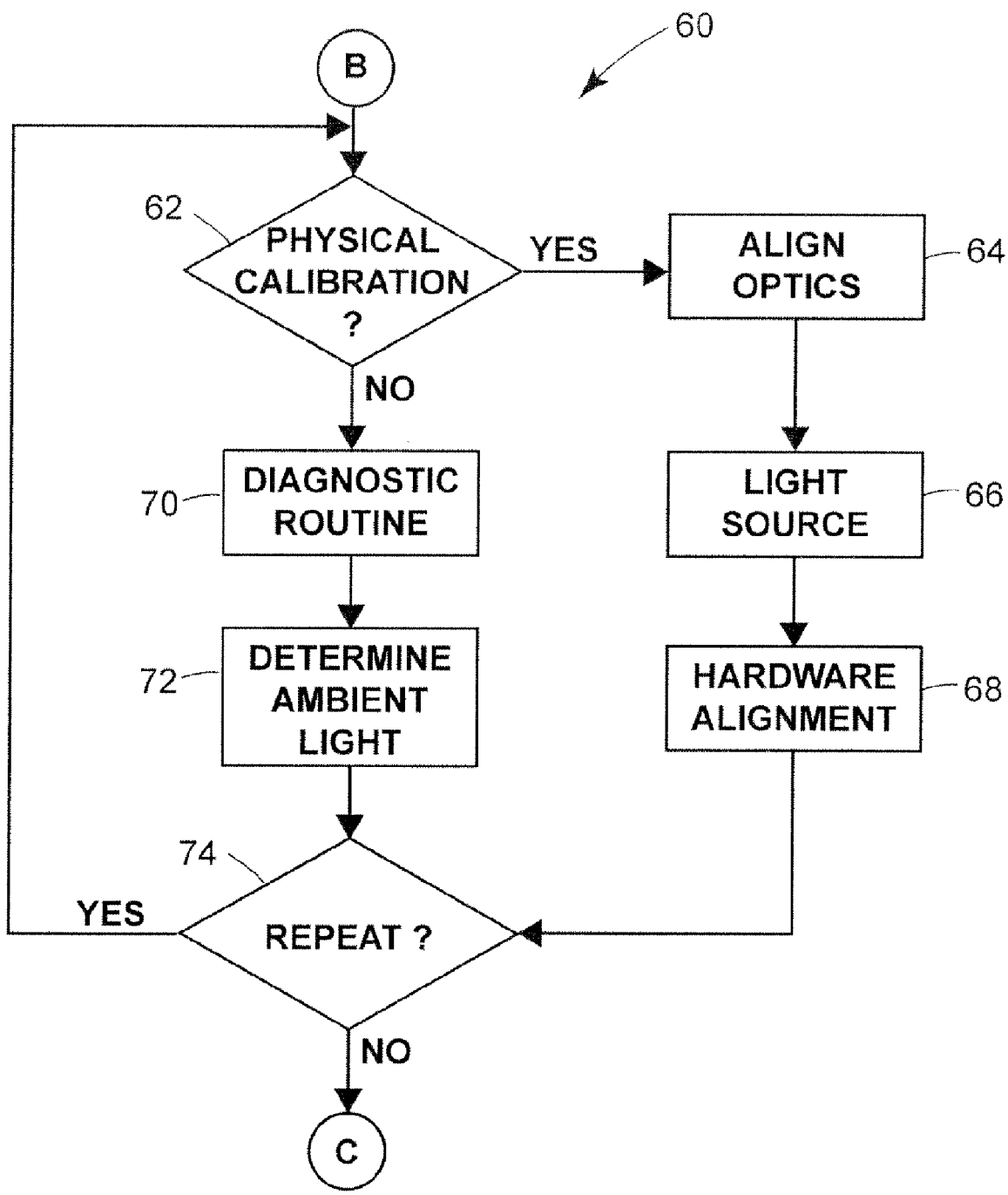
FIG. 3 illustrates a flowchart embodying the operation of an exemplary calibration routine.

FIG. 3 illustrates the calibration routine 60 that may be implemented at any point during the retinal evaluation method 40. At a block 62, a physical or software controlled calibration procedure can be performed depending upon a maintenance criterion or other selection mechanism. At a block 64, the optics and objective lens can be physically aligned by adjusting the positioning rack and pinion and/or by offsetting or shifting the initial position of a positioning servo or stepper motor. Further, the objective lenses may be rotationally shifted relative to each other to correct for any misalignment that can cause image distortion, blurriness, etc.

At a block 66, the output strength and alignment of the excitation light source can be evaluated. The excitation light source may include, for example, an internal photodiode that monitors the light intensity and that operates to correct any detected variations in the output strength. Further, the photodiode may simply provide a maintenance signal to indicate when the lamp needs to be replaced. At a block 68, testing hardware, such as a guide for the subject, stand height, chin rest, forehead rest, or other testing hardware can be adjusted or aligned.

At a block 70, software or electronic calibration may be performed by executing diagnostic routines native to the camera and/or the intensifier. These routines may, for example, compare the stored power levels to detected power levels generated by the CCD camera array in response to a known input. At a block 72, the ambient light present around the retinal evaluation equipment and especially the CCD camera may be measured. One possible manner of determining the ambient light may be to capture and evaluate a known image exposed to known lighting conditions with values stored within the CCD camera or another connected processor, or by using a light meter to detect background ambient light levels at the CCD camera. The difference, if any, between the stored and the evaluated values may then be used to offset the light and/or power levels of the CCD camera. At a block 74, the calibration process 60 may be repeated based on the calculated results or other calibration criteria such as, for example, minimum determined CCD intensity and/or excitation light source intensity. If the calibration procedure is not repeated, the method may return to the retinal evaluation routine 40 as indicated.

It will be understood that the exemplary retinal evaluation method 40 described above provides a non-invasive evaluation method that is clinically and experimentally useful because, among other things, the methodology is inexpensive, quick, and painless while requiring a minimum of patient effort. As discussed above, the endogenous fluorochrome flavoprotein (FP) provides an indication of the retinal metabolic activity within retinal cells and can be monitored in a reliable, non-invasive fashion.

Figure 1:
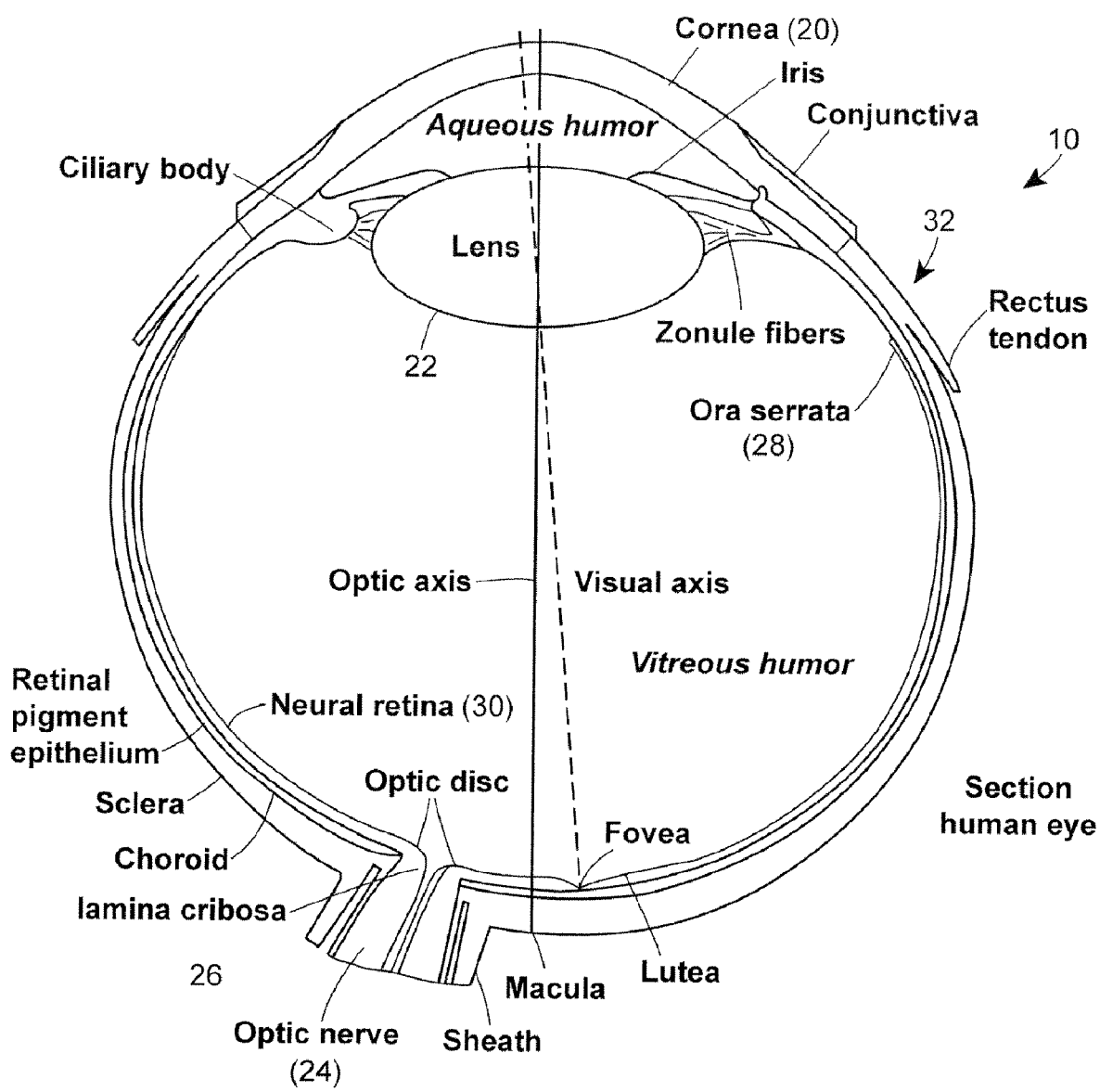
FIG. 1 illustrates a cross-sectional view of the components of an exemplary eye.

Preliminary studies of the exemplary evaluation method 40 illustrated in FIGS. 1 and 2 included performing in vitro studies on isolated retinal cells and ex vivo studies on two isolated human retinas. The in vitro experiments compared the auto-fluorescence excitation spectra of purified FP component and an unlabeled human leukocytes using a 530 nm emission wavelength. The excitation properties can be evaluated using a microfluorometry apparatus to perform excitation spectroscopy associated with the 530 nm excitation emission. The in vitro experiments confirmed that the emissions detected at the 530 nm, based on the correlation between the two samples, are likely to have originated with the auto-fluorescence of the flavoproteins (FPs) of interest.

The ex vivo experiments were performed on human retinal tissue having a high content of retinal pigment epithial (RPE) cells including oxidized, fluorescent melanin and dark granules. The physical experiment employed the OMEGA OPTI-CAL® Model No. XF1012 (455DF70) excitation filter in conjunction with a 495 nm long-pass dichroic reflector. It will be understood that filtered excitation means may be directed and delivered to the subject/patient using a fiber optic harness and system. Emission spectroscopy of the excited retinal tissue showed a peak at 530 nm, which has been identified as matching the known FP auto-fluorescence. These emission results were confirmed by examining the retinal emission spectra in the presence of a metabolic inhibitor, which caused an increase in FP auto-fluorescence, and in the presence of cyanide, which caused a reduction in FP auto-fluorescence. The results of these experiments confirmed that emission intensity of FPs relate inversely with the level of mitochondrial activity (e.g., an increase in metabolic activity results in a decrease in FP auto-fluorescence).

Figure 4:
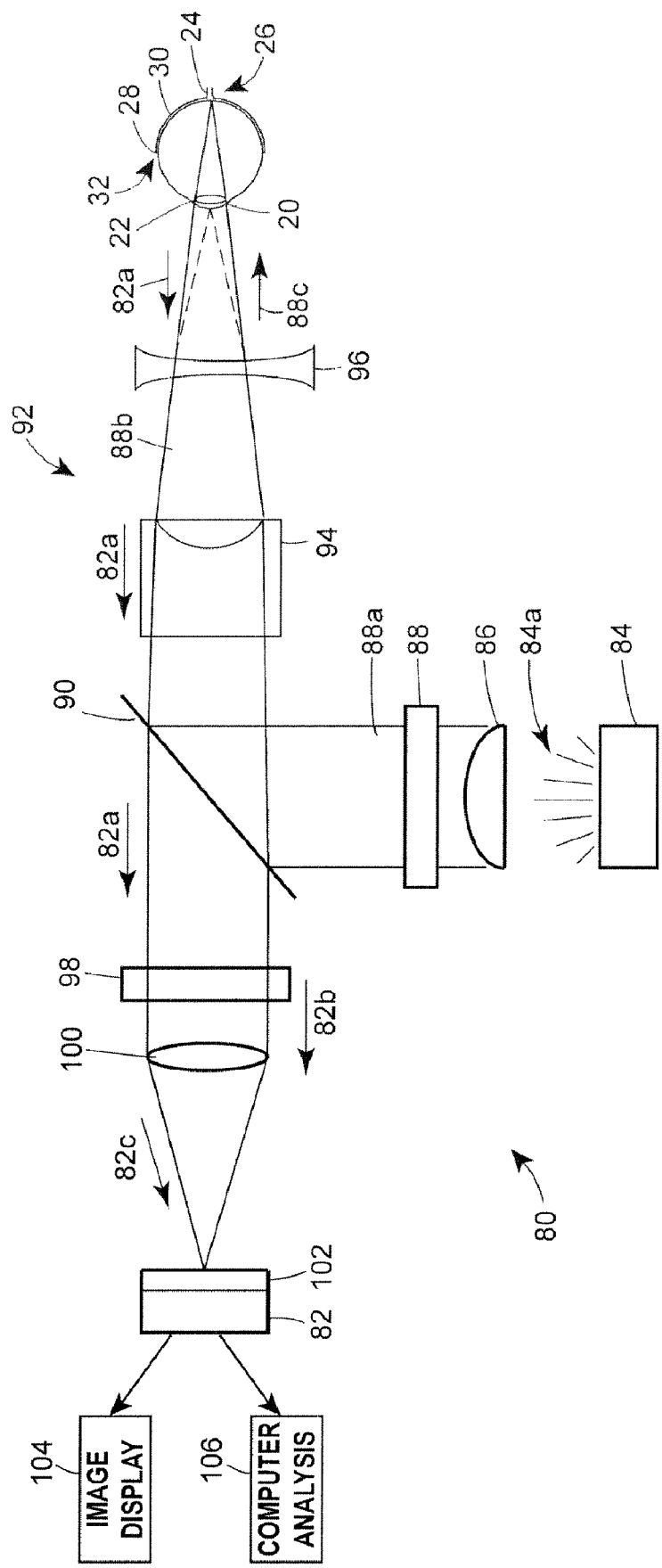
FIG. 4 illustrates the functional arrangement of a plurality of components included with an exemplary evaluation apparatus.

FIG. 4 illustrates an exemplary apparatus for performing retinal evaluations generally indicated by the numeral 80. Generally, the evaluation apparatus 80 includes a still camera, a charged coupled device (CCD) camera 82, and an excitation light source 84 arranged to capture a single image representing the FP auto-fluorescence present within the subject retina 30. If a CCD camera 82 is used, it may be, for example, a cooled CCD camera that may include a Peltier cooler to reduce the temperature of the detector and thereby decrease thermally generated electronic noise or dark current noise. As previously discussed, the retina 30 can be stimulated by the excitation light source 84 and the resulting FP auto-fluorescence can be recorded by the still camera or the CCD camera 82. It will be understood that the CCD camera 82 can be selected to have FOV optimized to capture the single image or in the case of a still camera, photographic image. Upon analysis, the image captured by the CCD camera 82 allows a direct and non-invasive procedure for determining the metabolic activity or health of the subject retina 30.

In operation, the excitation light source 84, which may be a mercury lamp such as an ATTOARC™ mercury lamp having a bright mercury line near 440 nm, or a laser of similar wave length, cooperates with a focusing lens 86 to direct the emitted excitation light 84*a* to an excitation filter 88. The excitation filter 88 may be, for example, the OMEGA OPTI-CAL® excitation filter described above and may be selected to prevent light of wavelengths beyond the range of approximately 400-500 nm from being transmitted to the subject retina 30. The filtered light 88*a* may then be directed to a dichroic reflector 90, such as the 495 nm long-pass dichroic reflector discussed above, for redirection towards the subject retina 30.

The redirected filtered light 88*b* may then pass through an optics stage 92 which may include a microscope objective 94 and a contact lens 96 or a fundus or slit-lamp camera apparatus. The microscope objective 94 and the contact lens 96 may act to focus, align and magnify the redirected filtered light 88*a* onto a desired area of the subject retina 30. It will be understood that under some test conditions, an applanation means such as a flat, optically clear lens or plane may be used to flatten or deform the cornea 20 to a desired shape to thereby allow better or more accurate imaging. Alternatively, an appropriate contact lens for fundus viewing may be employed.

The focused redirected light 88*c* illuminates the retina thereby causing auto-fluorescence of the associated flavoproteins (FPs). The generated FP auto-fluorescence 82*a* may be directed away from the subject retina 30 and through the components of the optics stage 92, and the dichroic reflector 90 to an emission filter 98 such as, for example, an OMEGA OPTICAL® Model No. XF3003 (520DF40). The emission filter 98 may be selected to prevent wavelengths that do not correspond to FP auto-fluorescence wavelength, (e.g., wavelengths of or around 530 nm) from passing through its structure. The filtered FP auto-fluorescence 82*b* may then pass through a focusing lens 100 which focuses FP auto-fluorescence 82*c* on the still camera or CCD camera 82. At this point the filtered FP auto-fluorescence 82*b* may be displayed on a video display unit 104 such as a LCD or cathode ray tube for visual evaluation, or may be communicated to a personal computer 106 for analysis, storage or other desired image processing.

The CCD camera 82 may further include and cooperate with an image intensifier 102 to magnify the brightness of the focused FP auto-fluorescence 82*c* to facilitate analysis of the captured image. The image intensifier 102 will likely be selected such that the gain, which is the ratio between the signal captured by the detector of the CCD camera 82 and the corresponding output signal, represents an increase of 100 to 1000 times the original image intensity. The image can be acquired, for example, by using a high-speed PRINCETON ST-133 interface and a STANFORD RESEARCH SYSTEMS® DG-535 delay gate generator with speeds ranging from 5 nsec to several minutes. The delay gate generator cooperates with the CCD camera 82 and the image intensifier 102 to synchronize and control the operation of these components. It will be understood that this captured image represents only the focused FP auto-fluorescence 82*c* in an intensified form, the unwanted auto-fluorescence information or noise having been minimized by the operation of the excitation filter 86 and the emission filter 98. In this manner, the resulting single image captured by CCD camera 82 has a high S/N ratio and provides a clear and detailed image representing the FP auto-fluorescence 82*a*-82*c*.

The components of the retinal evaluation apparatus 80 described herein may be used in a stand alone fashion, wherein alignment is accomplished via manual clamping and securing of the individual components. However, the imaging, excitation and optical components of the retinal evaluation apparatus 80 may be integrated into any known desktop or handheld ophthalmoscope, slit-lamp, or fundus camera, to allow easy upgrade to the testing equipment described herein. Specifically, the CCD camera 82, the excitation light source 84, the optics stage 92, and the associated components may each be equipped with an adaptor (not shown) designed to allow each of the individual components of the retinal evaluation apparatus 80 to be mated with the ophthalmoscopes and other devices discussed above. In this case, the standard ophthalmoscope, fundus, or slit-lamp light may be replaced with the excitation means 84 affixed to the ophthalmoscope frame using a bracket or adaptor and the light output by the excitation means 84 maybe filtered to produce the desired excitation light 84*a*. An image detection device may be attached to the frames of the devices and aligned opposite the retina 30 to detect a single image representing the FP auto-fluorescence generated in response to the excitation light 84*a*. In this manner, existing devices can be retrofitted to allow known diagnostic equipment to be used to excite and evaluate retinal auto-fluorescence.

Although certain retinal evaluation systems and methods have been described herein in accordance with the teachings of the present disclosure, the scope and coverage of this patent is not limited thereto. On the contrary, this patent is intended to cover all embodiments of the teachings of the disclosure that fairly fall within the scope of the permissible equivalents.

What is claimed is:

1. A device for measuring apoptotic activity of an eye, said device comprising:
   an excitation light source to provide an excitation light that maximizes the excitation of flavoprotein auto-fluorescence in a retina and minimizes the excitation of non-flavoprotein auto-fluorescence in the retina and
   image capture means for recording a single image representative of a retinal fluorescence signal generated immediately in response to the excitation light to minimize inaccuracies introduced by eye movements and rapid physiological changes, said image capture means including
   a filter to maximize the passage of flavoprotein auto-fluorescence in the retinal fluorescence signal and
   image intensifier means for providing a focused amplified image showing evidence of apoptotic activity in the eye and increase the retinal fluorescence signal strength.

2. The device of claim 1, wherein said excitation light source comprises a mercury lamp.

3. The device of claim 2, wherein said excitation light source comprises an excitation filter having a filter range corresponding to excitation of flavoprotein auto-fluorescence.

4. The device of claim 1, wherein said excitation light source comprises a laser.

5. The device of claim 1, wherein said excitation light source is aligned with the retina using a dichroic reflector.

6. The device of claim 1, wherein said excitation light source is aligned with the retina using a fiber optic system.

7. The device of claim 1, wherein said image capture means comprises a charge coupled device.

8. The device of claim 1, wherein said image capture means comprises a still camera.

9. The device of claim 1, wherein said image capture means comprises a charge coupled device camera.

10. The device of claim 1, wherein said image intensifier means includes a gain factor of at least 100.

11. The device of claim 1, wherein said image capture means has a field of view sized to capture a single image of the retinal fluorescence signal generated by the retina.

12. The device of claim 1, further comprising a processor programmed to analyze the retinal fluorescence signal with respect to a second stored retinal fluorescence signal.

13. The device of claim 1, further comprising a processor programmed to analyze the retinal fluorescence signal to determine a contrast change.

14. The device of claim 13, wherein said processor is programmed to analyze the retinal fluorescence signal to determine a local contrast change.

15. The device of claim 13, wherein said processor is programmed to analyze the retinal fluorescence signal to determine a rate of contrast change.

16. A method of noninvasively measuring apoptotic activity, the method comprising:

providing an excitation light generated by the excitation light source to induce retinal auto-fluorescence in a subject retina, wherein the excitation light maximizes the excitation of flavoprotein auto-fluorescence and minimizes the excitation of non-flavoprotein auto-fluorescence;

capturing a single image representing the induced retinal auto-fluorescence immediately, to minimize inaccuracies introduced by eye movements and rapid physiological changes, intensifying said immediately captured single image to increase the signal strength of the retinal autofluorescence; and analyzing said immediately captured single image to determine apoptotic activity.

17. The method of claim 16, including aligning a still camera.

18. The method of claim 16, including aligning an image intensifier.

19. The method of claim 16, including generating the excitation light at an excitation wavelength of about 460 nm.

20. The method of claim 16, further including reducing the amount of ambient light presented to the subject retina.

21. The method of claim 16, further including filtering the induced retinal autofluorescence to maximize the passage of flavoprotein auto-fluorescence and attenuate non-flavoprotein auto-fluorescence.

22. The method of claim 16, wherein capturing a single image includes capturing an image representative of the auto-fluorescence specific to flavoproteins.

23. The method of claim 16, further including analyzing the single image and comparing the single image with a second stored single image.

24. The method of claim 16, wherein analyzing the single image further includes determining a local contrast change.

25. The method of claim 16, wherein said step of analyzing the single image includes determining a rate of contrast change.

26. The method of claim 16, further including aligning at least one objective lens between an image detection device and the subject retina.

27. A method of upgrading a standard imaging device to non-invasively measure apoptotic activity of a retina, the method comprising:

replacing a standard light source with an excitation light source for generating a filtered excitation light that maximizes the excitation of flavoprotein auto-fluorescence and minimizes the excitation of non-flavoprotein autofluorescence;

positioning an image detection device to detect a single image representing a retinal auto-fluorescence generated in response to the filtered excitation light immediately, to minimize inaccuracies introduced by eye movements and rapid physiological changes; and increasing the intensity of the single image using an intensifier.

28. The method of upgrading a standard imaging device of claim 27, further comprising positioning a filter between the image detection device and a subject retina to maximize the passage of flavoprotein auto-fluorescence and attenuate non-flavoprotein auto-fluorescence.

29. The method of upgrading a standard imaging device of claim 27, wherein providing the excitation light source includes providing a mercury lamp.

30. The method of upgrading a standard imaging device of claim 27, wherein providing the excitation light source includes providing a laser.

31. The method of upgrading a standard imaging device of claim 27, wherein generating the filtered excitation light includes producing light at a wavelength of about 460 nm.

32. The method of upgrading a standard imaging device of claim 27, further comprising positioning at least one objective lens to scale the detected signal image.

* * * * *